United States Patent [19]

Chang et al.

[11] Patent Number: 4,654,312

[45] Date of Patent: Mar. 31, 1987

[54] LYSING AGENT FOR ANALYSIS OF PERIPHERAL BLOOD CELLS

[75] Inventors: Chin-hai Chang, Los Altos; Alex M. Saunders, San Carlos, both of Calif.

[73] Assignee: Becton, Dickinson and Company, Franklin Lakes, N.J.

[21] Appl. No.: 610,152

[22] Filed: May 14, 1984

[51] Int. Cl.[4] .................. G01N 33/554; G01N 31/00; G01N 1/00
[52] U.S. Cl. ....................................... 436/519; 436/10; 436/17; 436/522; 436/546; 424/3; 424/7.1; 252/408.1
[58] Field of Search ................. 436/17, 519, 546, 522, 436/10, 17; 252/408.1; 424/3, 7.1

[56] References Cited

U.S. PATENT DOCUMENTS

| | | | |
|---|---|---|---|
| 3,741,875 | 6/1973 | Ansley et al. | 252/408.1 X |
| 4,160,644 | 7/1979 | Ryan | 424/3 |
| 4,286,963 | 9/1981 | Ledis et al. | 252/408.1 X |
| 4,436,821 | 3/1984 | Ryan | 435/2 |

OTHER PUBLICATIONS

Ansley et al., Advances in Automated Analysis, 1970, pp. 437–446.

*Primary Examiner*—Christine M. Nucker
*Assistant Examiner*—Stephen C. Wieder
*Attorney, Agent, or Firm*—James R. McBride

[57] ABSTRACT

A lysing agent and a method for utilizing the lysing agent in the identification and enumeration of cells of a select subclass of leucocytes is provided. The lysing agent includes formaldehyde, an alkali or alkaline earth salt of a weak acid and a polyhydric alcohol.

20 Claims, 4 Drawing Figures

(A) Drawing of gating
    box around lymphocytes
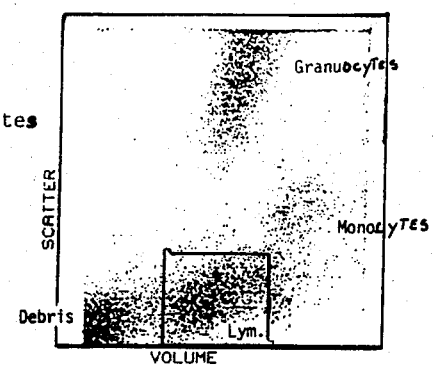
(B) Real-time gating
    on lymphocytes
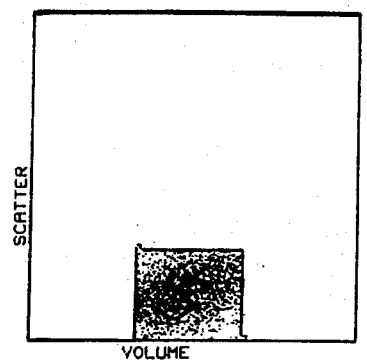
(C) FL1 vs. FL2 plot
    of gated lymphocytes
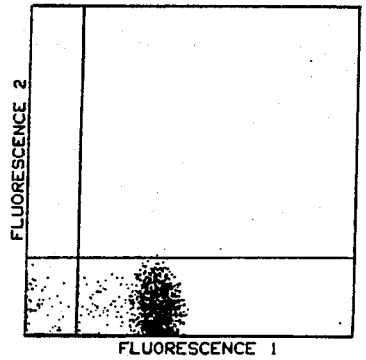
Quadrant count
  lower lft    155
  lower rght   3843
  upper lft    0
  upper rght   2
  total        4000
Quadrant Percentage
  upper left   0.0  upper right  0.1
  lower left   3.9  lower right  96.1
Fig.1      Whole blood stained with anti-HLe-1-FITC (A) Drawing of gating box around mononuclear cells
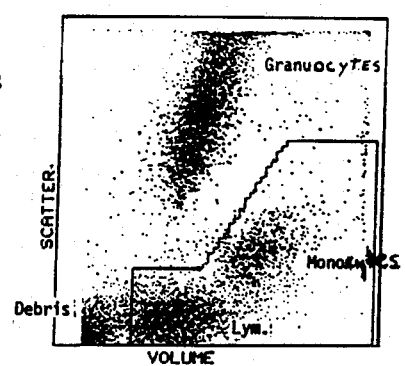
(B) Real-time gating on mononuclear cells
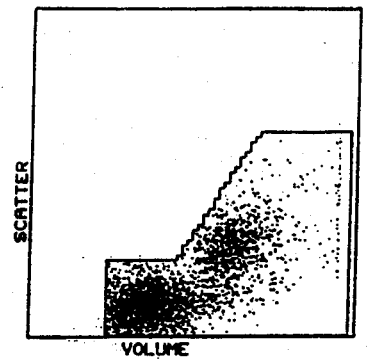
(C) FL1 vs. FL2 plot of gated mononuclear cells
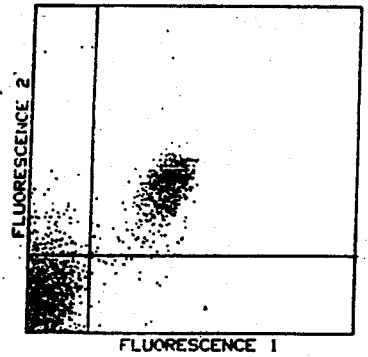
Quadrant count
```
    lower lft.   3896
    lower rght.    28
    upper lft.    191
    upper rght.   885
         total  5000
```
Quadrant Percentage
```
    upper left   3.8   upper right  17.7
    lower left  77.9   lower right   0.6
```
Fig. 2  Whole blood stained with anti-Leu M3-FITC and anti-Leu M3-PE

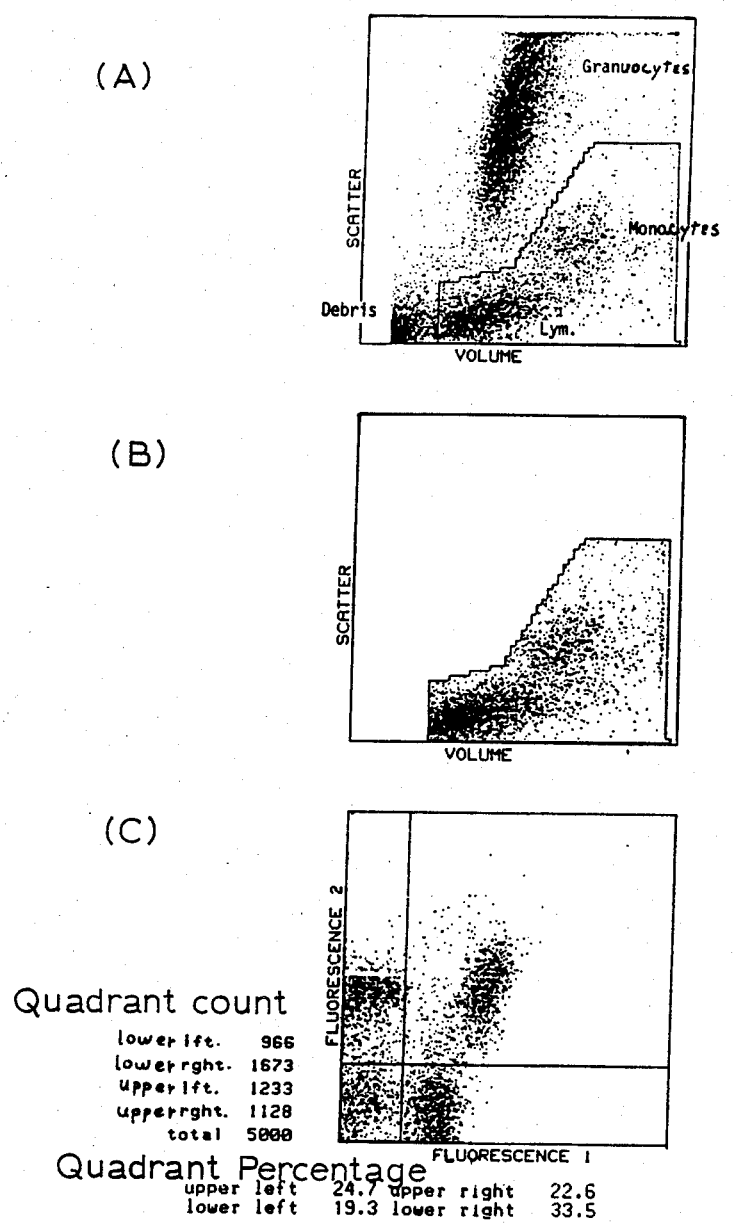
Fig. 3  Whole blood stained with anti-Leu M3-FITC, anti-Leu M3-PE, anti-Leu 2-PE and anti-Leu 3-FITC.

FACS IV resolution of whole blood sample processed with the lysing system

LYSING AGENT FOR ANALYSIS OF PERIPHERAL BLOOD CELLS

FIELD OF THE INVENTION

The present invention is directed generally to a lysing agent for use in the flow cytofluorimetric analysis of human peripheral blood cells. More particularly, the present invention is directed to a lysing agent which can be used with whole blood to mask the effect of erythrocytes during analysis of leukocytes by flow cytometric techniques.

BACKGROUND AND PRIOR ART

Blood is a fluid that contains a variety of cells. The most numerous cells (more than 90%) are the erythrocytes, or red blood cells, which carry out the exchange of oxygen and carbon dioxide between the lungs and the body tissues. The minor population of cells are the leucocytes, or white blood cells, which control the immuno response system of the body and defend the body against infecting organisms and foreign agents both in the tissues and the bloodstream.

The leucocyte population in blood is further defined by a number of subclasses which play distinct roles in the immune response. For example, the relative number cells in various subclasses of lymphocytes (about 20% of the leucocyte population) is likely to change in various disease states. Identification of cells of the various subclasses of lymphocytes provides an indication of the relative well being of the patient.

It is known that at least several particular subclasses of functionally distinct lymphocytes can be identified on the basis of antigenic determinants found on the cell surface. For example, the analysis of the T-cell population of the lymphocyte fraction of leukocytes is currently under intensive investigation in a wide variety of disease states. In renal allograft recipients, for example, monitoring of T-cell subsets in peripheral blood provides information which can be used as a basis for clinical decisions.; Cosimi, A.B., et al., 1981, N. Engl. J. Med. 14,308. Since significance is attached to relatively small changes in the sizes of the subpopulations of T-cells, it is necessary to have an accurate, reproducible method for obtaining data regarding the T-cell subpopulations.

It should be understood that there are two principal classes of lymphocytes involved in the immune system of humans and animals. The first of these (the thymus-derived cell or T-cell) have immunological specificity and are directly involved in cell-mediated immune responses (such as graft rejection). Although T-cells do not secrete antibodies, they are sometimes required for the effective secretion of these antibodies by the second class of lymphocytes discussed below. Some types of T-cells play a regulating function in other aspects of the immune system. The mechanism of this process of cell cooperation is not yet completely understood.

The second class of lymphocytes (the bone marrow-derived cells or B cells) are those which secrete antibody. It is thought that B cells differentiate within the bone marrow.

T-cells are divided into at least several subtypes, termed "helper", "suppressor", and "killer" T-cells, which have the function of (respectively) promoting a reaction, suppressing a reaction, or killing (lysing) foreign cells. These subclasses are well understood for murine systems, and have recently been identified for human systems. The ability to identify subclasses of T-cells is important for diagnosis or treatment of various immunoregulatory disorders or conditions.

Conventional immunofluorescence techniques presently includes the physical separation of the lymphocytes from other leukocytes and the erythrocytes as a preliminary step, usually by density gradient centrifugation (Boyum. A., 1968 Scand. J. Clin. Lab Invest., 21 Suppl. 97). This separation step eliminates the possibility that non-specifically stained monocytes or granulocytes might be counted as specifically stained lymphocytes. This initial lymphocyte isolation step is long and arduous; in fact much longer than the relatively simple step of tagging and analyzing the tagged lymphocytes. The necessity of separating the lymphocytes from other leukocytes and erythrocytes is a serious impediment to rapid clinical analyses. Furthermore, even for research applications, where time is less important, the lymphocyte separation steps involves the risk of loss of some lymphocytes which introduces uncertainty and inaccuracy to the subsequent analysis.

It is, accordingly, a primary object of the present invention to provide a method and lysing agent for identifying and enumerating specific subclasses of lymphocytes in a whole blood sample without the necessity for prior separation of lymphocytes from other blood cells.

It is another object to provide methods and a lysing agent enumerating various subclasses of lymphocytes which are more accurate and precise than present techniques, and which substantially prevent faulty analysis due to the presence of erythrocytes or loss of data through loss of lymphocytes from the sample.

It is a further object to provide such methods wherein the speed and relative simplicity of the method makes lymphocyte subclass identification and enumeration of a viable clinical tool.

SUMMARY OF THE INVENTION

U.S. Pat. No. 4,284,412 to Hansen et al. is directed to an apparatus and method whereby a whole blood sample can be utilized in an analysis for specific subclasses of the leucocytes. In the method of the Hansen et al. patent, an aliquot of whole blood is provided. The whole blood sample is selectively tagged so that a select subclass of leucocytes is provided with a marker to distinguish the select class of leucocytes. The tagging is preferably accomplished by incubating the aliquot with an antibody which is selectively reactive with distinct antigenic determinants on the surface of cells of the select subclass. The antibody is provided with a predetermined fluorescence which responds to a given optical stimulation. The erythrocytes are then lysed so as to break the erythrocytes into fragments. The aliquot, containing the leucocyte population of which a select subclass has been tagged, is then passed, substantially a cell at a time, through an area of focused optical stimulation so as to determine the cells which have been tagged with the antibody while detecting light scattered by and emitted from the cells. The cells of the selected subclass are differentiated from other cells based at least in part on occurrence of the predetermined fluorescence response to the optical stimulation.

A problem encountered with using the method of the Hansen et al. patent is the selection of a lysing agent. The lysing agent should be sufficiently strong to lyse substantially all of the erythrocytes while not being sufficiently strong to lyse any of the leukocytes. The lysing agent should also be capable of preserving the leukocytes during the lysing step, that is to spare the leukocytes from destruction. In essence, a race occurs after addition of the lysing agent whereby destruction of the erythrocytes proceeds concurrently with destruction and preservation of the leucocytes. Any substantial destruction of the leukocytes and any nonsubstantial retention of the erythrocytes results in providing a sample that is not suitable for analysis by flow cytometric techniques.

The present invention is directed to providing a lysing agent for whole blood which substantially lyses the erythrocyte fraction of whole blood while retaining and fixing the leukocyte fraction. The lysing agent is an aqueous solution of a short chain aliphatic aldehyde, such as formaldehyde, and alkali or alkaline earth salt of a weak acid, such as sodium citrate and a polyhydric alcohol, such as diethylene glycol.

DESCRIPTION OF THE DRAWINGS

FIGS. 1-4 are representations of flow cytometric charts prepared utilizing the lysing agent of the invention. The sample, after lysing of the erythrocytes, is analysed by flow cytometry techniques.

Figure 4:
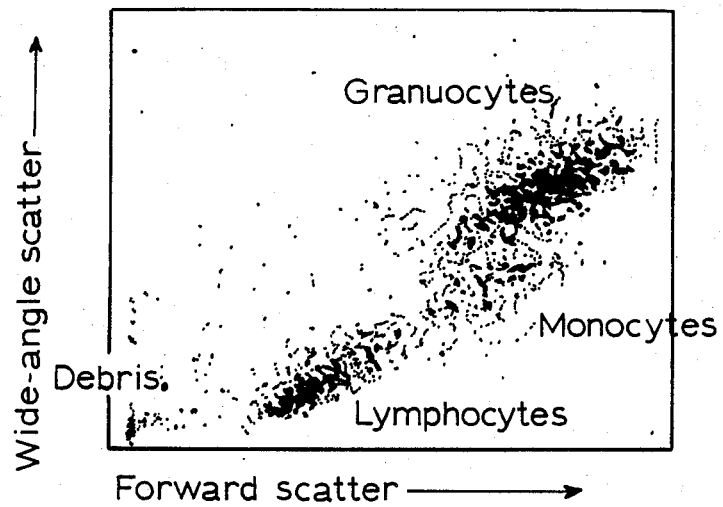

As used herein, flow cytometry is defined as a rapid single cell measuring device, whereby cells in suspension pass single file through a part at which electronic volume as well as wide angle scatter and one or more fluorescence measurements are made simultaneously.

DETAILED DESCRIPTION OF THE INVENTION

Preparation of a blood sample in accordance with the principles of the present invention usually first involves incubation of a blood sample with an antibody which has been suitably tagged with a fluorescent marker and which is capable of recognizing an antigenic site on a cell in a subclass of interest. Particularly suitable antibodies for purposes of preparation of the blood sample include monoclonal antibodies which are obtained from a hybrid cell line. Suitable monoclonal antibodies are available which recognize the various subsets of T-cells forming a subpopulation of lymphocytes. Other monoclonal antibodies are available which recognize other such monoclonal antibodies are commericially available which have been previously conjugated to suitable fluorescent markers. A single blood sample aliquot may be incubated simultaneously with multiple monoclonal antibodies with one or more than one fluorescent species.

After the blood sample has been incubated with a suitable antibody, the erythrocytes are lysed from the sample using the lysing agent of the present invention. The lysing agent also permits the clean identificatfon of the three major non-erythrocyte cells in blood---granulocytes, monocytes and lymphocytes, without addition of any tag or identifying reagent, by physical means alone. That is, the cells, after action of the lysing agent, can be classified into granulocytes, monocytes and lymphocytes (and debris or other) by use of electronic volume and wide angle scatter alone.

In accordance with the invention, the erythrocytes are lysed under mild hypotonic conditions while the leukocytes are spared from destruction by mild simultaneous fixing. A solution containing from about 0.5 to about 4 percent of a short chain aliphatic aldehyde having a carbon chain length of from 1 to 4 preferably formaldehyde in distilled water is capable of lysing the erythrocytes with substantial recovery of leukocytes. In this system, the aldehyde acts as a fixing agent to stabilize the white cells while the distilled water acts as a lysing agent to rupture the erythrocytes to become "ghosts", which are empty sacks, as they are more susceptible to the hypotonic shock. The concentration of aldehyde is important in this system. Too much aldehyde (over 4 percent) prevents some erythrocytes from lysis; while too little aldehyde (less than 0.5 percent) results in destruction of some leukocytes.

To accomplish the objectives of the invention of providing an improved direct whole blood test for identification and enumeration of specific leukocytes or their subsets by flow cytometry, further optimization of the lysing condition is necessary to prevent the residual ghosts in the lysed and washed sample from interfering with the analysis. The residual ghosts sometimes provide a "smearing" effect on the electronic volume obtained and partially overlap with the leukocyte subset under investigation. It has been found that the inclusion of a polyhydric alcohol, such as glycerol, diethylene glycol or polyethylene glycol, along with addition of certain alkali or alkaline earth salts of weak acids so as to raise the pH to a level of about 6.5 to about 8.5 dramatically improves the resolution by electronic volume, of various cell sizes. Suitable alkali and alkaline earth salts of weak acids include the sodium or potassium salts of citrate, phosphate, acetate, formate, ascorbate and bicarbonate. The polyhydric alcohol is preferably present at a level of from about 1 to about 6 percent. The alkali or alkaline earth salt of a weak acid is preferably present at a level of from about 0.1 to about 1 percent. All percentages set forth herein are by weight, unless specifically noted otherwise.

A most preferred lysing system in accordance with the invention contains about one percent formaldehyde, about 0.25 percent sodium citrate and about 3 percent diethylene glycol with the balance being distilled water. The pH is from about 7.2 to about 8.2. Using this lysing system, the lymphocyte cluster becomes much tighter and more clearly separated from the blood debris in the electronic volume measuring system. When examined on a two dimensional dot plot of electronic volume vs wide angle scatter, the granulocyte cluster appears to be more compact and further separated from lymphocytes and monocytes. The lysing stream also does not "quench" fluorescent markers, such as fluorescein isothiocyanate (FITC) and phycoerytherin (PE) proteins, which are frequently used to label antibodies for studying cell surface markers by flow cytometry.

In accordance with the invention, it is possible to stain whole blood samples with the fluorescent labeled antibodies directed to specific cell surface markers followed by adding the lysing system to lyse all erythrocytes and simultaneously fix all leukocytes. After one washing with buffered saline, the blood sample is ready for analysis by flow cytometry using a cytometer equipped with electronic volume and with wide angle scatter.

In essence, the present invention provides a lysing system which offers the following important features:

1. The lysing condition is sufficiently mild that it does not disrupt the delicate cell surface markers subsequent to tagging the markers with a fluorescent labeled antibody and erythrocyte lysis.

2. The lysing condition has no adverse effect on the antibody fluorescence.

3. The lysing system not only lyses all erythrocytes but also renders all ghosts in a condition clearly separated from the lymphocytes when analyzed by flow cytometry. Thus, "gating" of the lymphocytes is more free from interference by debris. As used herein, gating means isolation of a portion of the sample by electronic logic based on one or more physical measurements.

4. The granulocytes provided by the lysing system of the present invention form a very compact cluster which can be readily "gated" to eliminate their interference in analysis of monocytes and lymphocytes by flow cytometry.

5. Simultaneous fixing of the leukocytes during lysis renders the stained leukocytes more stable and thus permits ample time for analysis.

6. The blood sample prepared in accordance with the invention provides excellent resolution, not only on a flow cytometer that measures cell size based on the "Coulter volume" principle, but also on a flow cytometer which measures size by forward light scatter. The lysing system of the present invention thus has a wide application potential to the state of the art of current flow cytometry.

EXAMPLES

Example 1

(A) Sample Preparation (1) Incubate 50 l whole blood with 5 l of anti-HLe1-FITC (a monoclonal antibody that stains all leukocytes but no red cells or platelets) in an ice bath for 30 minutes.

(2) Add 2 ml of the lysing solution (1% formaldehye. 3% diethylene glycol, 0.25% sodium citrate, pH 7.7+0.5) and further incubate at room temperature for 10 minutes.

(3) Centrifuge at 300×g for 3 minutes at 4°-20° C. Remove the supernatant by aspiration.

(4) Add 3 ml sheath fluid (a buffered isotonic saline) and centrifuge at 300×g for 3 minutes at 4°-20° C. Remove the supernatant by aspiration.

(5) Add 0.3 ml sheath fluid containing 0.5% formaldehyde and read the tube on a flow cytometer.

(B) Analysis by Flow Cytometry

A FACS Analyzer available from the FACS division of Becton, Dickinson and Company is used here for illustration. The FACS Analyzer is equipped with a wide-angle scatter detector and determines cell size by the electronic volume principle. The FACS Analyzer is coupled with software which acquires data in list mode and permits realtime gating of a particular cell type(s) in the wide-angle scatter vs. volume plot, followed by display of the FL1 (first fluorescence channel) vs. FL2 (second fluorescence channel) plot of the gated events. FIG. 1A shows the good resolution of the three main while cell types: granulocyte (Gran.), monocyte (Mono.) and lymphocyte (Lym.) in the lysed sample. There is a clear separation between lymphocytes and debris, thus permitting easier drawing of the "gating" box around lymphocytes. FIG. 1B shows the result of subsequent real-time gating on lymphocytes, and FIG. 2C is the FL1 vs. FL2 plot of the gated events. Only less than 4% of total events (the lower-left box of FIG. 1C) in the lymphocyte gate did not stain anti-HLe-1-FITC. As a control, the mononuclear cells (monocytes and lymphocytes) separated from erythrocytes by the standard ficoll-hypaque procedure were also subjected to the same staining and analysis. Similarly only 4% of total events in the lymphocyte gate did not stain anti-HLe-1-FITC. Thus, the resolution of the whole blood protocol using the developed lysing solution, as far as clean lymphocyte cluster is concerned, matches the result of using purified cells.

Example 2

Stain 50 l blood with 5 l anti-Leu M3-FITC (green fluorescence) and anti-Leu M3-PE (red fluorescence) simultaneously, and then follow the procedure in Example 1 to lyse the red cells with the lysing solution and test the processed sample on the FACS Analyzer. Anti-Leu M3 is a monoclonal antibody active in detecting mature monocytes. To determine the quantity of monocyte (as percent of total mononuclear cells) with the system, one can draw a "gating" box around monocytes and lympocytes together as shown in FIG. 2A. The subsequent real-time gating on the mononuclear cells (FIG. 2B) yielded 17.7% of the gated events as doubly stained cells (monocytes) in the upper-right box of the FL1 vs. FL2 plot (FIG. 2C). This represents 17.7% of the mononuclear cells in the sample as monocyte. The result was comparable to the mononuclear cells separated from the same blood sample and stained and analyzed in a similar manner. This demonstrates that the whole blood test using the lysing system of the invention achieved the same degree of accuracy as using the purified mononuclear cells in the quantitation of monocytes.

Example 3

Stain 50 l blood with 5 l anti-Leu M3-FITC, 5 l anti-Leu M3-PE, 5 l anti-Leu 2-PE and 5 l anti-Leu 3-FITC simultaneously, and then follow the procedure in Example 1 to lyse red cells with the lysing solution and test the processed sample on the FACS Analyzer. Anti-Leu 2 stains the suppressor T-cells while anti-Leu 3 stains the helper T-cells. When the monocytes and lymphocytes (mononuclear cells) were gated as in Example 2, there is obtained, not only 22.6% monocyte (stained in both red and green), but also 24.7% suppressor T-cell (stained in red only) and 33.5% helper T-cell (stained in green only) in the FL1 vs. FL2 plot simultaneously (FIG. 3). This result was comparable to the separated mononuclear cells when the same antibody stains were applied. This demonstrates again that the lysing system can facilitate simultaenous analysis of monocytes, lymphocytes and their subsets in a direct whole blood protocol using the FACS Analyzer type of flow cytometer. Thus, prior separation of mononuclear cells by laborious procedures is no longer required.

Example 4

FIG. 4 shows the FACS IV resolution of a whole blood sample that was processed according to the procedure in Example 1. The FACS IV is a laser-based flow cytometer that measures cell size by forward light scatter. The separation distance between lymphocytes and debris is significantly greater by FACS IV than by FACS Analyzer. This demonstrates that the red cell lysing system developed works well for the direct whole blood test with both kinds of flow cytometers which determine cell size by either electronic volume principle or forward light scatter.

What is claimed is:

1. In a method of identifying and enumerating cells of a select subclass of non-erythrocyte particulate components in blood wherein an aliquot of a blood sample to be studied is provided, a select subclass of non-erythrocyte particulates is selectively tagged by incubating the aliquot with an antibody which is selectively reactive with distinct antigenic targets on the surface of the select subclass, the antibody having a predetermined fluorescence response to a given optical stimulation, the erythrocytes in the aliquot are lysed, the aliquot is passed, substantially a particle at a time through an area of focused optical stimulation while detecting light scattered by and emitted from the particle and the particles of the selected subclass are differentiated based at least in part on comparison of the predetermined fluorescence response in the detected light, the improvement comprising utilizing a lysing agent comprising the mixture of an aqueous solution of:
   a. a short chain aliphatic aldehyde with carbon chain length of one to four
   b. an alkali or alkaline earth salt of a weak acid, and
   c. a polyhydric alcohol 2. The method in accordance with claim 1 wherein said aldehyde is selected from the group consisting of formaldehyde and butryaldehyde.

3. The method in accordance with claim 1 wherein said alkali or alkaline earth salt of a weak acid is selected from the group consisting of sodium and potassium salts of citrate, phosphate, acetate, formate, ascorbate and bicarbonate.

4. The method in accordance with claim 1 wherein said polyhydric alcohol is selected from the group consisting of glycerol, diethylene glycol and polyethylene glycol.

5. The method in accordance with claim 1 wherein said formaldehyde is present at a level of from about 0.5 to about 4 percent.

6. The method in accordance with claim 1 wherein said alkali or alkaline earth salt of a weak acid is present at a level of from about 0.1 to about 1 percent.

7. The method in accordance with claim 1 wherein said polyhydric alcohol is present at a level of from about 1 to about 6 percent.

8. The method in accordance with claim 1 comprising a mixture of any aqueous solution of formaldehyde, diethylene glycol and sodium citrate.

9. The method in accordance with claim 8 wherein said formaldehyde is present at a level of from about 0.5 to about 4 percent, said sodium citrate is present at a level of from about 0.1 to about 1.0 percent and said diethylene glycol is present at a level of from about 1 to about 6 percent.

10. The method in accordance with claim 8 wherein said formaldehyde is present at a level of about 1 percent, said sodium citrate is present at about 0.25 percent and said diethylene glycol is present at a level of about 3 percent.

11. A method for identification of subclasses of leucocytes comprising:
   (a) providing an aliquot of a whole blood sample;
   (b) lysing erythrocytes in said aliquot with a lysing agent which comprises an aqueous solution of a short chain aliphatic aldehyde having a carbon chain length of from 1 to 4, an alkali or alkaline earth salt of a weak acid and a polyhydric alcohol;
   (c) passing said aliquot substantially a particle at a time through an area of focused optical illumination and detecting the electronic volume and light scattered by the particles; and
   (d) differentiating particles of a subclass of leucocytes at least in part on the basis of said electronic volume and said light scatter.

12. A method in accordance with claim 11 wherein said aldehyde is selected from the group consisting of formaldehyde and butryaldehyde.

13. A method in accordance with claim 11 wherein said alkali or alkaline earth salt of a weak acid is selected from the group consisting of sodium and potassium salts of citrate, phosphate, acetate, formate, ascorbate and bicarbonate.

14. A method in accordance with claim 11 wherein said polyhydric alcohol is selected from the group consisting of glycerol, diethylene glycol and polyethylene glycol.

15. A method in accordance with claim 11 wherein said aldehyde is present at a level of from about 0.5 to about 4 percent.

16. A method in accordance with claim 11 wherein said alkali or alkaline earth salt of a weak acid is present at a level of from about 0.1 to about 1 percent.

17. A method in accordance with claim 11 wherein said polyhydric alcohol is present at a level of from about 1 to about 6 percent.

18. A method in accordance with claim 11 comprising a mixture of an aqueous solution of formaldehyde, diethylene glycol and sodium citrate.

19. A method in accordance with claim 18 wherein said formaldehyde is present at a level of from about 0.5 to about 4 percent, said sodium citrate is present at a level of from about 0.1 to about 1.0 percent and said diethylene glycol is present at a level of from about 1 to about 6 percent.

20. A method in accordance with claim 18 wherein said formaldehyde is present at a level of about 1 percent, said sodium citrate is present at about 0.25 percent and said diethylene glycol is present at a level of about 3 percent.

* * * * *